(12) United States Patent
Ukaj

(10) Patent No.: US 8,566,993 B1
(45) Date of Patent: Oct. 29, 2013

(54) SPLATTER CONTROLLING TOOTH POLISHING SYSTEM

(76) Inventor: Theresa Luz Ukaj, Pompano Beach, FL (US)

(*) Notice: Subject to any disclaimer, the term of this patent is extended or adjusted under 35 U.S.C. 154(b) by 272 days.

(21) Appl. No.: 13/157,731

(22) Filed: Jun. 10, 2011

Related U.S. Application Data

(63) Continuation-in-part of application No. 11/440,281, filed on May 24, 2006, now Pat. No. 7,958,588.

(60) Provisional application No. 60/752,549, filed on Dec. 21, 2005.

(51) Int. Cl.
*A61C 1/16* (2006.01)
*A61C 3/06* (2006.01)

(52) U.S. Cl.
USPC .............. 15/28; 15/97.1; 433/116; 433/125

(58) Field of Classification Search
USPC ................ 15/22.1, 28, 97.1; 433/116, 125
See application file for complete search history.

(56) References Cited

U.S. PATENT DOCUMENTS

| | | | |
|---|---|---|---|
| 1,694,636 A | 12/1928 | Barker | |
| 2,039,278 A * | 5/1936 | Blanchard | 15/188 |
| 3,195,537 A * | 7/1965 | Blasi | 601/114 |
| 3,621,577 A * | 11/1971 | Spinello | 433/166 |
| 3,939,599 A * | 2/1976 | Henry et al. | 433/99 |
| 4,274,173 A * | 6/1981 | Cohen | 15/28 |
| 4,424,036 A * | 1/1984 | Lokken | 433/116 |
| 5,131,846 A * | 7/1992 | Hall | 433/116 |
| 5,380,202 A | 1/1995 | Brahler | |
| 5,584,690 A * | 12/1996 | Maassarani | 433/125 |
| 5,642,995 A * | 7/1997 | Bailey | 433/115 |
| 5,775,905 A | 7/1998 | Weissenfluh et al. | |
| 2006/0292522 A1 * | 12/2006 | Lees et al. | 433/116 |

* cited by examiner

*Primary Examiner* — Randall Chin
(74) *Attorney, Agent, or Firm* — Allen D. Hertz, P.A.; Allen D. Hertz

(57) ABSTRACT

A variable speed tooth polishing system including a tooth polisher with multiple polishing head capability, in order to provide therapeutic treatment to gums and guard against undesired exposure to potentially hazardous fluids present during routine dental cleansing and polishing, such as polishing paste, tooth paste, blood, and salivary excretions. A splatter guard comprising a plurality of serrations are cut through a wall of the splatter guard, wherein each of the serrations starting at an open end of the splatter guard and continuing into a length of said splatter guard forming a series of flexible splatter guard fingers about the open end of the splatter guard. The splatter guard is affixed to a polishing end of a prophy angle encompassing a polisher, wherein the splatter guard is provided to entrap any loose material resulting from a polishing process within the splatter guard.

20 Claims, 9 Drawing Sheets

SPLATTER CONTROLLING TOOTH POLISHING SYSTEM

CROSS-REFERENCE TO RELATED APPLICATION

This Continuation-In-Part Patent Application claims the benefit of United States Provisional patent application Ser. No. 11/440,281, filed May 24, 2006 (Issuing on Jun. 14, 2011 as U.S. Pat. No. 7,958,588), which claims benefit to then United States Provisional Patent Application Ser. No. 60/752,549, filed Dec. 21, 2005 (now expired), which are all incorporated herein in their entireties.

BACKGROUND OF THE INVENTION

1. Field of the Invention

The present invention relates generally to a variable speed tooth polishing system containing two polishing heads for added stability on the teeth, that can be used to massage the gums, while at the same time providing hygienic protection against the mess created by the spraying of fluids during dental cleaning, such as polishing paste, tooth paste, saliva, and blood.

2. Description of the Prior Art

Oral disease has plagued human beings since the beginning of history, but it wasn't until dentistry advanced to the stage of detecting bacteria responsible for periodontal disease, that preventive dentistry became important. Detecting bacteria was further fueled by public concern regarding the risks of contracting infectious diseases through dental procedures, which in turn, has created an increased awareness and desire for more sophisticated dental equipment to better maintain teeth, for health, as well as aesthetic reasons.

Existing dental cleaners and polishers, however, are not without their disadvantages. To begin with, current polishers usually provide just one polishing head. This type of configuration has a tendency of rendering the polishers unstable, as they do not get adequate hold on the teeth and gums during the vibrating created by the rotating motion of the motor.

Furthermore, the bulkiness of existing polisher heads is not very comfortable when inserted into the mouth, limiting access to hard to reach teeth. This discomfort can lead to a shortened amount of cleansing and polishing time because of the user's inability to endure the process for extended lengths of time, which in turn results in deficient dental hygiene.

Moreover, standard polishers tend to have a power switch, which activates rotation at one particular speed. This is especially troublesome in situations where less force is required, as in the case of a child, or higher speeds are necessitated, by adults with more serious cleaning issues.

Additionally, current polishers do not provide adequate protection from the risks of potentially infectious fluids emanating from the patients mouth. As a result, users are exposed to such potentially harmful materials as saliva, blood, pastes, and other dental waste materials.

Another disadvantage of existing polishers is the inability of the polishing heads to remove food particles from between the teeth and gums. This is an important concern because a leading cause of periodontal disease is lack of flossing, which leads to plaque deposits and tooth decay.

Yet another disadvantage of standard polishers is that they concentrate on the teeth alone. Since the health of gums is just as important as the teeth themselves, overlooking care to this area can also lead to serious dental health issues that should be addressed as part of any preventative regimen.

With yet another limitation, existing polishers do not offer the option of interchangeable prophy angles. Because of this, users with various needs not addressed by a specific polishing device are forced to utilize multiple prophy angles, if they desire to receive optimum results, both hygienically and aesthetically.

Finally, when cleaning, polishing, and the like a patient's teeth, the rotational motion of the polisher or brush creates a centrifugal force which sends particulate matter flying. The strewn particulate matter, referred to as splatter, can cause several undesirable circumstances, including a soiling the patients, body, clothing, and the like; causing potential health risks by spewing biological particulate matter, including biological cells, blood, and the like; and other undesirable scenarios.

Accordingly, there is an established need for a variable speed tooth polishing system that, in addition to being constructed in a smaller, more adaptable manner, also provides safeguards against infectious materials and unhygienic messes, and which contains multiple polishing brushes that provide a firmer, more efficient grip on the teeth during the dental cleaning/polishing procedure.

SUMMARY OF THE INVENTION

The present invention is directed to a variable speed tooth polishing system. The tooth polisher of the present invention is configured for facilitating dental care by incorporating a more practical size, shape, and functionality into a simple to use mechanism, which takes into consideration aesthetic, as well as hygienic issues.

An aspect of the present invention is to provide a variable speed tooth polishing system that utilizes a single or multi-brush system comprising a splatter guard surrounding a rotation brush.

In yet another aspect, the tooth polishing system includes a proper amount of protection against exposure to adverse materials.

In yet another aspect, a splatter guard having a series of serrations cut through the sidewall of the splatter guard starting at an open end of said splatter guard and continuing into a length of said splatter guard forming a series of flexible splatter guard fingers about said open end which entrap any loose material resulting from a polishing process within the splatter guard.

In yet another aspect, the variable speed tooth polishing system massages the gums, while simultaneously buffing teeth for a more aesthetically pleasing appearance.

In yet another aspect, a variable speed tooth polishing system is provided comprising a prophy angle containing dual polishers that can be used in unison, or individually.

In yet another aspect, a splatter guard is provided that encases the polishers, in order to prevent users from being exposed to unsanitary byproducts during the dental cleaning procedure.

In yet another aspect, therapeutic massage is rendered to the gums by means of the polishers, promoting dental health and well-being.

In yet another aspect, the unique prophy angle polisher of the variable speed tooth polishing system is capable of being separated from the hand grip and utilized with other motorized dental cleaning aids.

In yet another aspect, a variable speed tooth polishing system is provided with multi-speed capability, in order to address the individual needs of users who require minimum, medium, or maximum rotational force of the polishers.

These and other aspects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, in which.

Like reference numerals refer to like parts throughout the several views of the drawings.

DETAILED DESCRIPTION OF THE PREFERRED EMBODIMENTS

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention is generally directed towards a variable speed tooth polishing system, designed specifically to provide users with a practical and efficient means for practicing dental hygiene in a compact, flexible structure that takes into consideration dental aesthetics, gum maintenance, and minimization of contact with potentially infectious substances.

Figure 1:
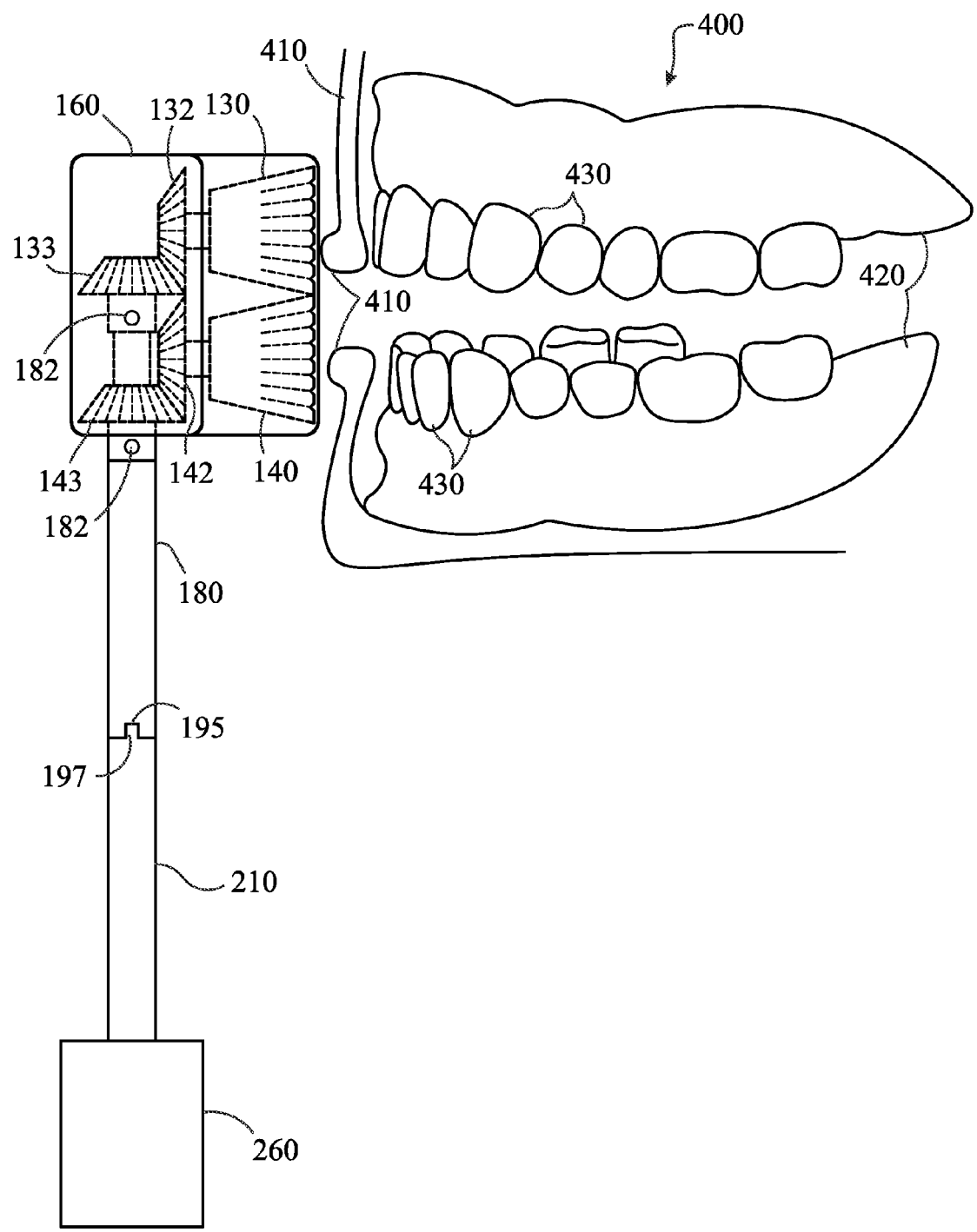
FIG. 1 is a left side view of the variable speed tooth polishing system, depicting the prophy angle, polisher, inner gears, before it is placed in the mouth.
Figure 2:
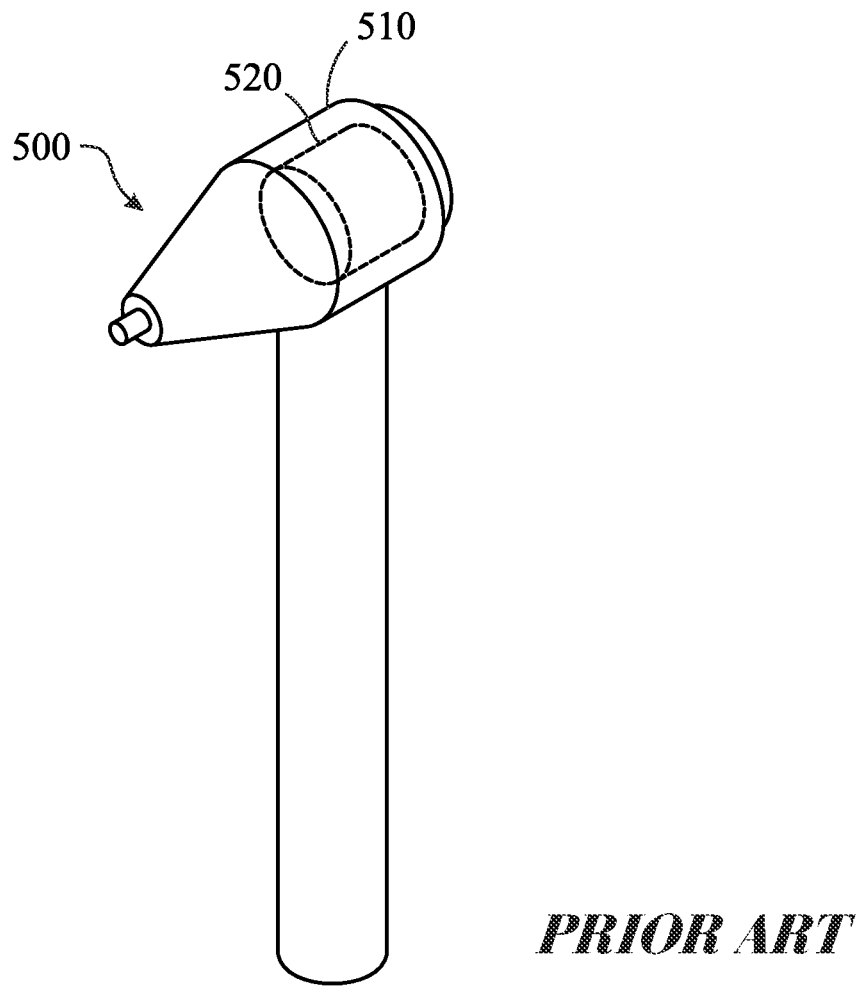
FIG. 2 is a front perspective view of a prior art polisher.
Figure 3:
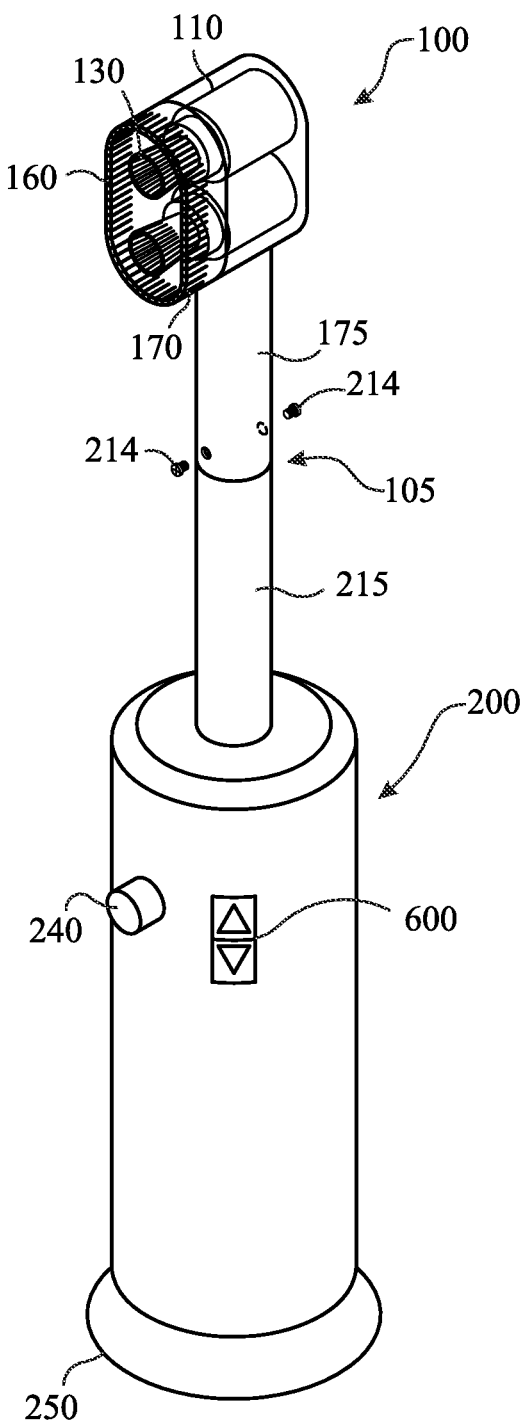
FIG. 3 is a front perspective view of a variable speed tooth polishing system with the prophy angle attached.

An exemplary prophy angle 105 and respective variable speed tooth polishing system 100 are presented in FIGS. 1 through 3. The prophy angle 105 of a variable speed tooth polishing system 100 is shown before it has been inserted into the mouth 400, past the lips 410 in order to make contact with the gums 420 and teeth 430. The prophy angle 105 includes are a first polisher 130, a first polisher gear 132, a first drive gear 133, a second polisher 140, a second polisher gear 142, a second drive gear 143, and a splatter guard 160. A prophy angle 500, in accordance with the known prior art, includes a polisher head 510, which contains within its structure a polisher motor 520, as illustrated in FIG. 2. The prophy angle 105 may be secured to a polisher hand grip 200 by threading at least one set screw 214 through the prophy angle connector housing 175 into a hand grip connector housing 215. These screws 214 will "preferably" be made of a non-corrosive material, such as plastic. The first polisher 130 is provided in the form of a prophy cup, a pointed polisher, such as the pointed polisher offered by Young Dental, and the like.

Figure 4:
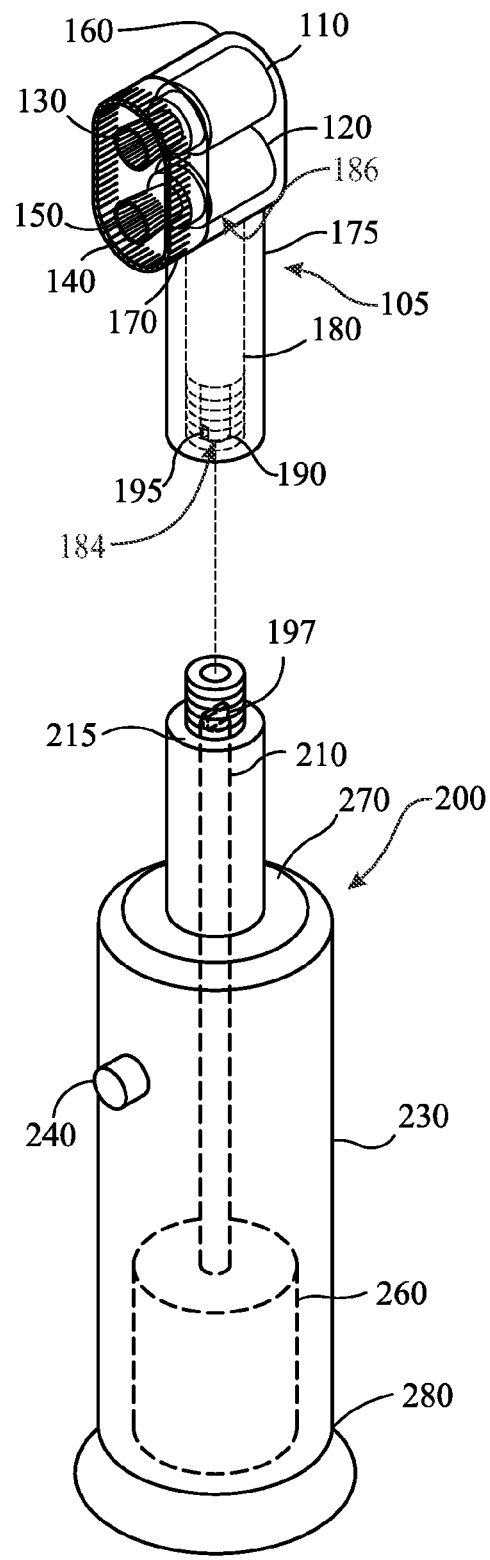
FIG. 4 is a partially exploded front perspective view of a variable speed tooth polishing system with a prophy angle removed from a hand grip.

The variable speed tooth polishing system 100 is shown with the prophy angle 105 separated from a polisher hand grip 200 is presented in FIG. 4. The prophy angle 105 includes a prophy angle connector housing 175 and the polisher hand grip 200 includes a hand grip connector housing 215. The prophy angle 105 is connected to the hand grip connector housing 215 by screwing the hand grip connector housing 215 and a threaded assembly portion 190 of the prophy angle connector housing 175 together. It is understood that the assembly interface can be of any releasably engaging interface, including the threaded interface as illustrated, a quick disconnect, a bossed interface, and the like. The interface can be keyed to ensure repeatable orientation between the prophy angle 105 and the polisher hand grip 200. A prophy angle shaft 180 is rotationally assembled within an interior section of the prophy angle connector housing 175. The prophy angle shaft 180 can be defined by a shaft drive attachment end 184 and a shaft polisher propelling end 186. The prophy angle shaft 180 includes a drive slot 195 at the shaft drive attachment end 184, which is sized and shaped to receive a drive tongue 197 extending from an end of a hand grip connector shaft 210. The hand grip connector shaft 210 extends from a motor 260. The first and second drive gears are attached to the prophy angle shaft 180 with set screws 182 or the like. It is understood that the hand grip connector shaft 210 is exemplary and the hand grip connector shaft 210 can be any prophy angle drive assembly for receiving the prophy angle 105. The threaded assembly portion 190, or any other form factor of a re-engageable connection interface, attaches to a mating interface provided by the prophy angle drive assembly. The drive slot 195, or any other form factor of a drive engaging feature, engages with a respective drive feature of said prophy angle drive assembly.

It will be appreciated by those skilled in the art that these structural elements of the present invention may be formed out of natural and synthetic materials, such as plastic, rubber, and combinations thereof, or any of a wide variety of other known materials without departing from the present invention. The figures illustrate the use of threads to connect the prophy angle 105 to the polisher hand grip 200, but may include any suitable removable assembly method, such as any type of fastener.

Also illustrated in the figures is a more detailed view of the prophy angle 105, showing the first polisher 130 inserted into a first polisher housing 110 and a second polisher 140 inserted into the second polisher housing 120. Both the first polisher 130 and the second polisher 140 include a plurality of polisher serrations 150 to enable more stable and thorough contact with the teeth 430 and gums 420. The first and second polishers are preferably fabricated from a flexible material. A splatter guard 160 can be provided in an oval shape encompassing the first polisher 130 and the second polisher 140. A plurality of splatter slots 170 is formed around a perimeter of the splatter guard 160. The splatter guard 160 is preferably fabricated from a flexible material. It is preferable that the plurality of splatter slots 170 is 5 mm to 7 mm long, but could be any suitable length. The plurality of polisher serrations 150 is preferably no more than 3 mm in length.

The polisher hand grip 200 includes a hand grip body 230, a power button 240, the motor 260, a hand grip top portion 270 and a handgrip bottom portion 280. The hand grip top portion 270 terminates a top of the hand grip body 230 and the handgrip bottom portion 280 terminates a bottom of the hand grip body 230. The motor 260 is retained in the hand grip body 230. The power button 240 controls the flow of electrical power to the motor 260. When the motor 260 is activated by the power button 240, the hand grip connector shaft 210 revolves, which turns the prophy angle shaft 180. Rotation of the prophy angle shaft 180 causes the first and second drive gears to rotate the first and second polisher gears, respectively. Spinning of the first and second polishers polishes the teeth 430 and massages the gums 420. The polisher hand grip 200 also contains the hand grip speed control 600, which regulates the rotational speed.

Figure 5:
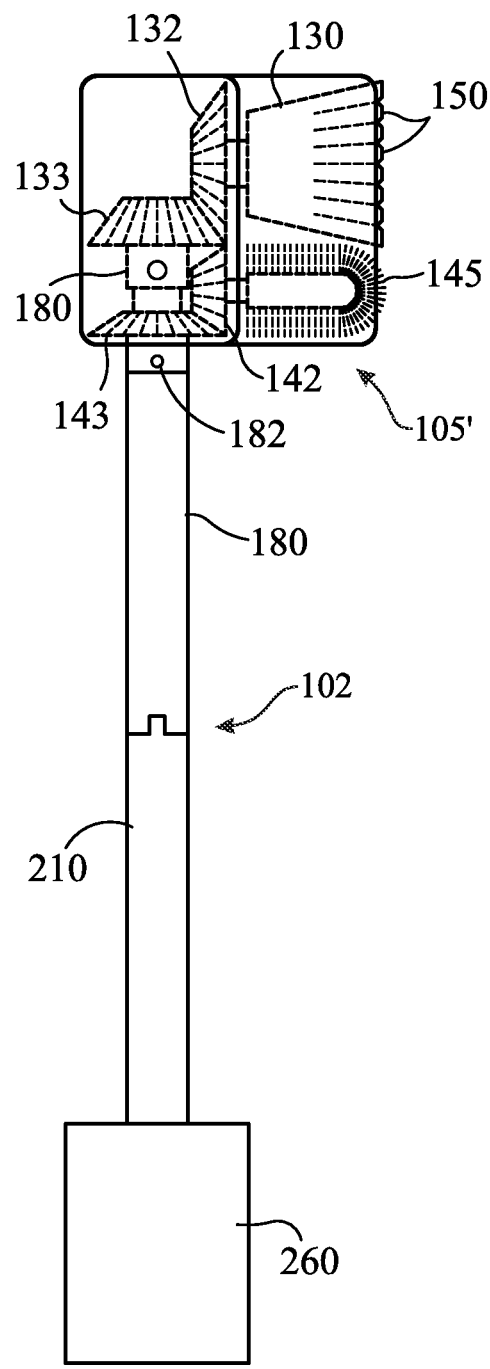
FIG. 5 is a left side view of a second embodiment of a variable speed tooth polishing system showing, wherein one polisher is replaced with a brush.
Figure 6:
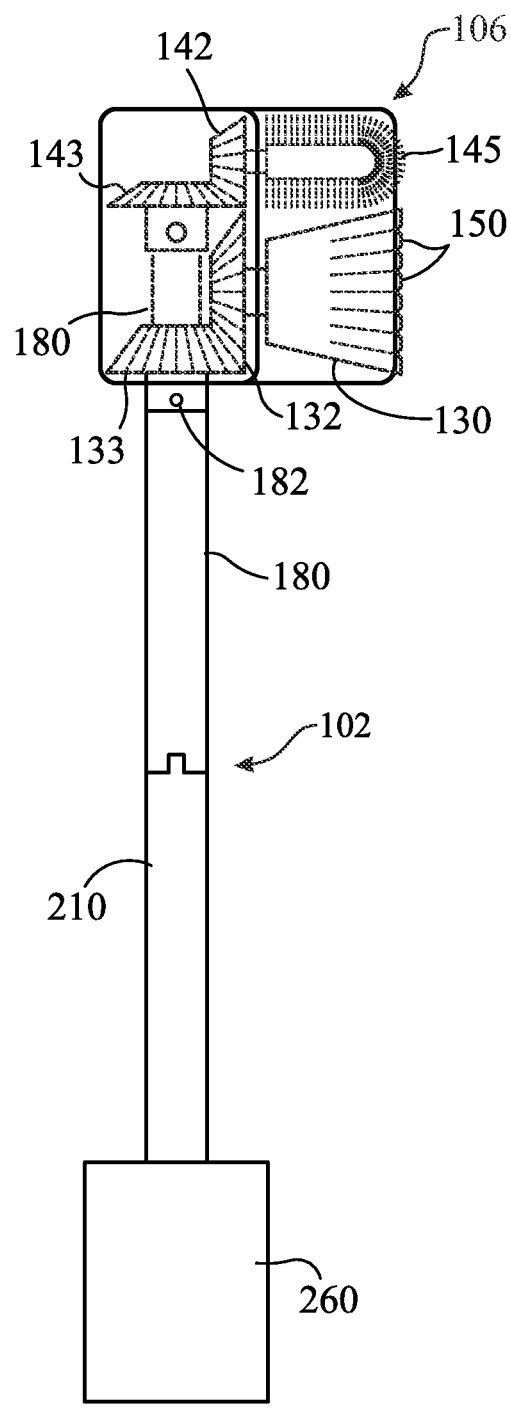
FIG. 6 is a left side view of a second embodiment of a variable speed tooth polishing system showing, wherein one polisher is replaced with a brush in an alternate location.

A second exemplary embodiment of a variable speed tooth polishing system 102 is presented in FIGS. 5 and 6. The variable speed tooth polishing system 102 is shown with the second polisher 140 replaced by a polisher brush 145. It will be appreciated by those skilled in the art that an elongated prophy angle 106 of the variable speed tooth polishing system 102 can be attached to other polisher hand grips, and that the first polisher 130 and the second polisher 140 can be removed and either act alone in order to access hard to reach teeth, or be replaced with other variations besides the polisher brush 145, without deviating from the present invention. A first exemplary configuration is presented in FIG. 5, positioning the polisher serrations 150 in a distal position and the polisher brush 145 in a proximal position, being closer to the polisher hand grip 250. A second exemplary configuration is presented in FIG. 6, positioning the polisher brush 145 in a distal position and the polisher serrations 150 in a proximal position, being closer to the polisher hand grip 250. The variable speed tooth polishing system 102 may be designed where one of the first polisher 130 and the polisher brush 145 may be operational and the second of the first polisher 130 and the polisher brush 145 remains stationary. This can be accomplished by the inclusion of any of a variety of designs. A first exemplary drive system utilizes a prophy angle shaft 180 which is hollow operationally engaged with a drive gear 133, 143 in a lower position and an internally located drive shaft located within the hollow interior of the prophy angle shaft 180, the internally located drive shaft operationally engaged with a drive gear 133, 143 in an upper position. The drive system engages with the hollow prophy angle shaft 180, the internally located drive shaft, or both. A second method allows for removal and reinstallation of either the first polisher 130 or the polisher brush 145.

Another alternative embodiment would entail the first polisher 130 and the second polisher 140 having a plurality of bristles, like those of a toothbrush, or a wide variety of other polishing means without departing from the present invention.

Figure 7:
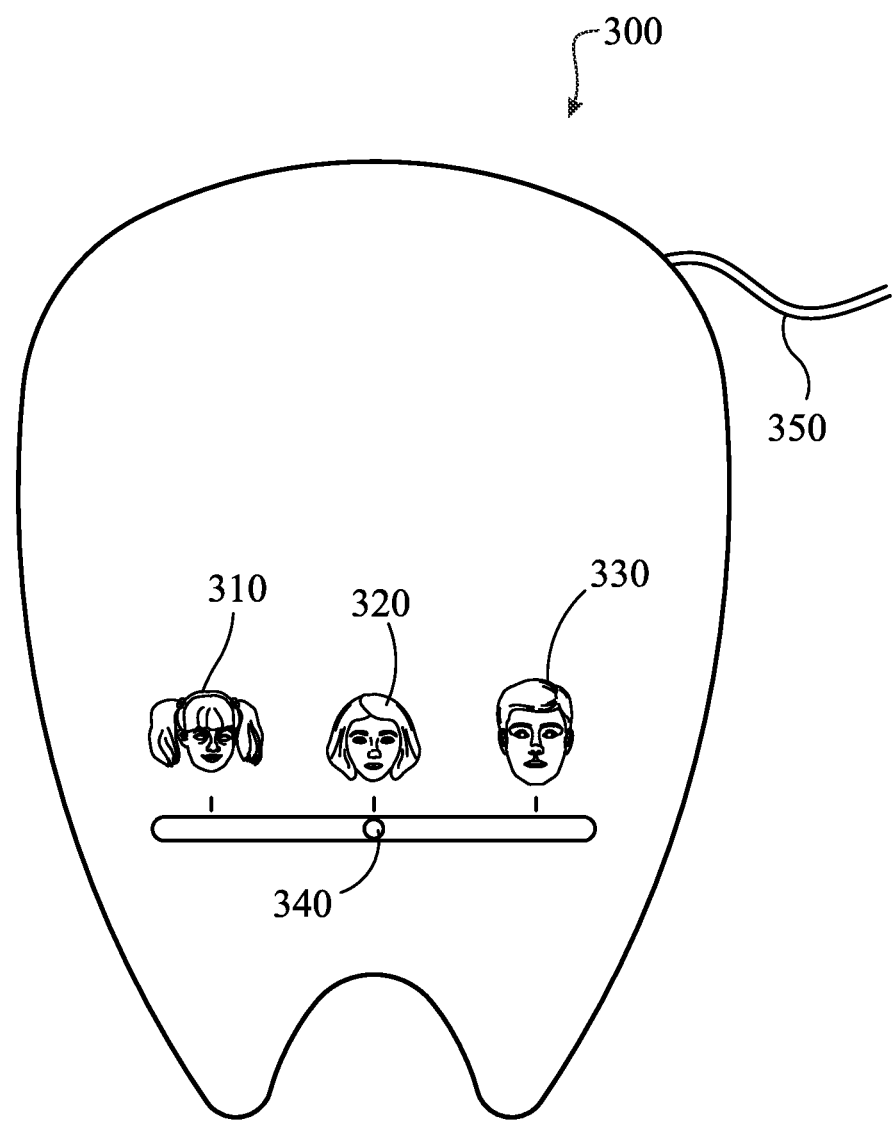
FIG. 7 is a front view of a control unit depicting variable speed input, as well as a wire that connects the control unit to a polisher hand grip.

An exemplary control unit 300 of the variable speed tooth polishing system 100, 102 is illustrated in FIG. 7. The control unit 300 determines the rotational speed of the first polisher 130 and second polisher 140 by movement of an indicator switch 340 to either the first setting indicator 310 (low speed), the second setting indicator 320 (medium speed), or the third setting indicator 330 (high speed). It is attached to the polisher hand grip 200 via a wire 350.

Figure 8:
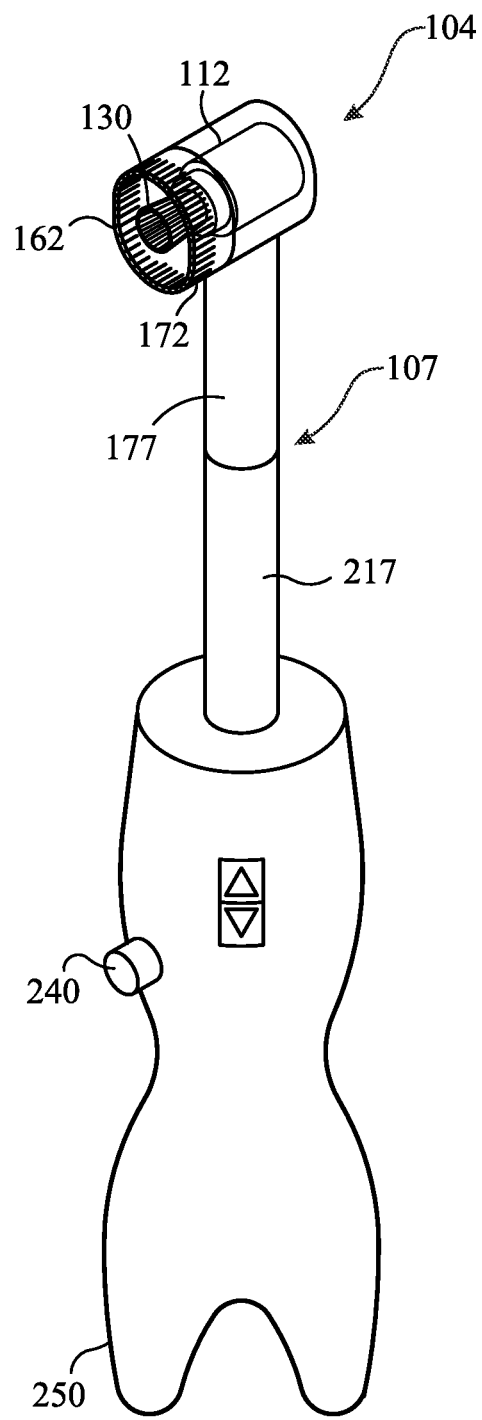
FIG. 8 is a perspective view of a third embodiment of a variable speed tooth polishing system with a single polisher.

A third exemplary embodiment of a variable speed tooth polishing system 104 comprising a single polisher 130 is presented in FIG. 8. The variable speed tooth polishing system 104 includes a polisher hand grip 250 and a prophy angle 107. A hand grip connector housing 217 extends from the polisher hand grip 250. The prophy angle 107 includes a prophy angle connector housing 177 and a splatter guard 162. The prophy angle connector housing 177 is preferably screwed to the hand grip connector housing 217, but other attachment methods may also be used. A polisher housing 112 is retained in the splatter guard 162. A plurality of splatter slots 172 is formed in a front of the splatter guard 162. The polisher is retained in the polisher housing 112.

Figure 9:
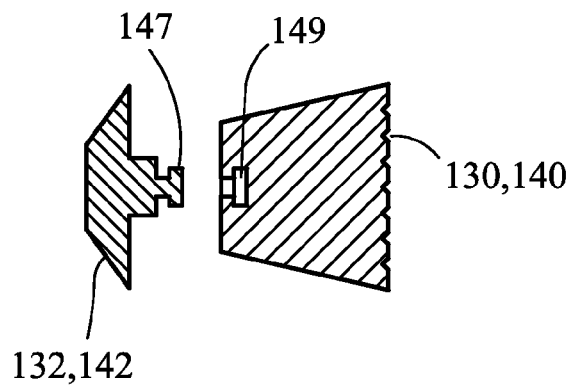
FIG. 9 is a cross-sectional view of a bevel gear having an undercut projection and a polisher having an undercut cavity for receiving the undercut projection of a variable speed tooth polishing system.
Figure 10:
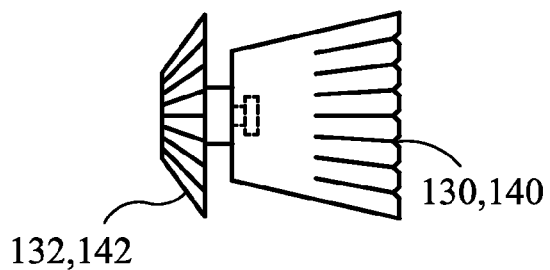
FIG. 10 is a cross-sectional view of a bevel gear having an undercut projection and a polisher having an undercut cavity for receiving the undercut projection assembled together of a variable speed tooth polishing system.
Figure 11:
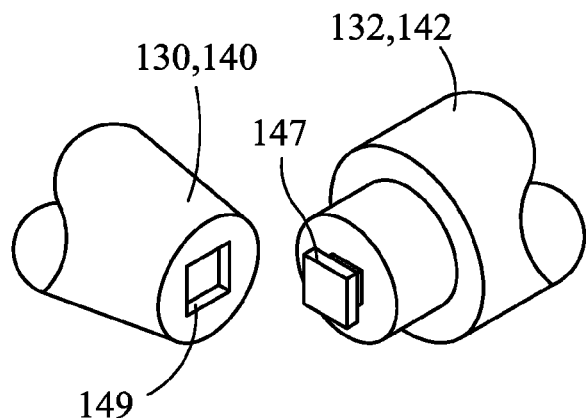
FIG. 11 is an enlarged perspective view of an undercut projection and an undercut cavity for receiving the undercut projection adjacent to each other of a variable speed tooth polishing system.

A method of attaching a polisher 130, 140 to a polisher gear 132, 142, respectively is illustrated in FIGS. 9 through 11. An undercut projection 147 extends from the polisher gear 132, 142. A projection cavity 149 is formed in a rear of the polisher 130, 140. The projection cavity 149 is sized to receive insertion of the undercut projection 147. After insertion of the undercut projection 147, the polisher 130, 140 is turned 45 degrees relative to the polisher gear 132, 142 to retain thereof relative to each other. However, other methods of removably attaching the polisher 130, 140 to the polisher gear 132, 142 may also be used. It is understood that the polisher 130, 140 may be removably attached to the polisher gear enabling the user to remove and replace the polisher 130, 140 with the same or a different form factor.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

The invention claimed is:
1. A tooth polishing assembly comprising:
a prophy angle comprising:
   a hollowed prophy angle housing, said prophy angle housing having a polishing end and a connection end;
   a prophy angle shaft being rotationally assembled within said prophy angle housing, said shaft having a shaft drive attachment end and a shaft polisher propelling end;
   a re-engageable connection interface integrated into said prophy angle housing connection end, said re-en- gageable connection interface is designed to mate with a mating interface of a prophy angle drive assembly;

a drive engaging feature provided at said shaft drive attachment end for engaging with a respective drive feature of said prophy angle drive assembly, causing said prophy angle shaft to rotate when in use;

at least one drive gear carried by said prophy angle shaft at said shaft polisher propelling end at least one drive gear;

at least one polisher gear rotationally assembled to a polishing end of said prophy angle housing, said at least one polisher gear is positioned engaging with each said at least one drive gear;

at least one polisher, wherein each polisher is individually assembled to respective polisher gear;

a splatter guard being formed as a continuous wall encompassing said at least one polisher; and a plurality of axial serrations being formed about a perimeter of said splatter guard, said plurality of axial serrations are cut through a wall of said splatter guard, said serrations starting at an open end of said splatter guard and continuing into a length of said splatter guard forming a series of flexible splatter guard fingers about said open end which entrap any loose material resulting from a polishing process within the splatter guard, wherein said prophy angle is designed to be removably attached to said prophy angle drive assembly at a fixed configuration, said drive assembly then rotates said prophy angle drive shaft, which in turn rotates said at least one polisher assembly, and said splatter guard is designed to have a flexible open end to contour to a contacting surface and retain any spewn material therein.

2. A tooth polishing assembly as recited in claim 1, further comprising:
a pair of polishers and a pair of polisher gears.

3. A tooth polishing assembly as recited in claim 2, wherein:
said splatter guard is provided in an oval shape encompassing said pair of polishers.

4. A tooth polishing assembly as recited in claim 1, further comprising:
a pair of polishers comprising a first polisher and a second polisher, wherein said first polisher is provided in a first polisher form factor and a second polisher is provided in a second polisher form factor, wherein said first polisher form factor and said second polisher form factor are dissimilar.

5. A tooth polishing assembly as recited in claim 4, wherein said first polisher form factor is a prophy cup and said second polisher form factor is a polisher brush.

6. A tooth polishing assembly as recited in claim 1, wherein said at least one polisher is removably assembled to said at least one polisher gear.

7. A tooth polishing assembly as recited in claim 1, further comprising a power source integrated into said prophy angle drive assembly.

8. A tooth polishing assembly comprising:
a prophy angle comprising:
a hollowed prophy angle housing, said prophy angle housing having a polishing end and a connection end;
a prophy angle shaft being rotationally assembled within said prophy angle housing, said shaft having a shaft drive attachment end and a shaft polisher propelling end;

a re-engageable connection interface integrated into said prophy angle housing connection end, said re-engageable connection interface is designed to mate with a mating interface of a prophy angle drive assembly;

a drive engaging feature provided at said shaft drive attachment end for engaging with a respective drive feature of said prophy angle drive assembly, causing said prophy angle shaft to rotate when in use;

at least one drive gear carried by said prophy angle shaft at said shaft polisher propelling end at least one drive gear;

at least one polisher assembly, each said at least one polisher assembly comprising a polisher assembled to a polisher gear, each at least one polisher assembly rotatably assembled to a polishing end of said prophy angle housing, each at least one polisher gear positioned engaging with each at least one respective drive gear;

a splatter guard being formed as a continuous wall encompassing said at least one polisher; and a plurality of axial serrations being formed about a perimeter of said splatter guard, said plurality of axial serrations are cut through a wall of said splatter guard, said serrations starting at an open end of said splatter guard and continuing into a length of said splatter guard forming a series of flexible splatter guard fingers about said open end which entrap any loose material resulting from a polishing process within the splatter guard, wherein said prophy angle is designed to be removably attached to said prophy angle drive assembly at a fixed configuration, said drive assembly then rotates said prophy angle drive shaft, which in turn rotates said at least one polisher assembly, and said splatter guard is designed to have a flexible open end to contour to a contacting surface and retain any spewn material therein.

9. A tooth polishing assembly as recited in claim 8, further comprising:
a pair of polishers and a pair of polisher gears.

10. A tooth polishing assembly as recited in claim 9, wherein:
said splatter guard is provided in an oval shape encompassing said pair of polishers.

11. A tooth polishing assembly as recited in claim 8, further comprising:
a pair of polishers comprising a first polisher and a second polisher, wherein said first polisher is provided in a first polisher form factor and a second polisher is provided in a second polisher form factor, wherein said first polisher form factor and said second polisher form factor are dissimilar.

12. A tooth polishing assembly as recited in claim 11, wherein said first polisher form factor is a prophy cup and said second polisher form factor is a polisher brush.

13. A tooth polishing assembly as recited in claim 8, wherein said at least one polisher is removably assembled to said at least one polisher gear.

14. A tooth polishing assembly as recited in claim 8, further comprising a power source integrated into said prophy angle drive assembly.

15. A tooth polishing assembly comprising:
a prophy angle comprising:
a hollowed prophy angle housing, said prophy angle housing having a polishing end and a connection end;

a prophy angle shaft being rotationally assembled within said prophy angle housing, said shaft having a shaft drive attachment end and a shaft polisher propelling end;

a re-engageable connection interface integrated into said prophy angle housing connection end, said re-engageable connection interface is designed to mate with a mating interface of a prophy angle drive assembly;

a drive engaging feature provided at said shaft drive attachment end for engaging with a respective drive feature of said prophy angle drive assembly, causing said prophy angle shaft to rotate when in use;

at least one drive gear carried by said prophy angle shaft at said shaft polisher propelling end at least one drive gear;

at least one polisher gear rotationally assembled to a polishing end of said prophy angle housing, each polisher gear positioned engaging with each respective drive gear;

at least one polisher, wherein each at least one polisher is individually assembled to each respective at least one polisher gear;

a splatter guard being formed as a continuous wall encompassing said at least one polisher; and a plurality of axial serrations being formed about a perimeter of said splatter guard, said plurality of axial serrations are cut through a wall of said splatter guard, said serrations starting at an open end of said splatter guard and continuing into a length of said splatter guard forming a series of flexible splatter guard fingers about said open end which entrap any loose material resulting from a polishing process within the splatter guard, wherein said prophy angle is designed to be removably attached to said prophy angle drive assembly at a fixed configuration, said drive assembly then rotates said prophy angle drive shaft, which in turn rotates said at least one polisher assembly, and said splatter guard is designed to have a flexible open end to contour to a contacting surface and retain any spewn material therein, and wherein said splatter guard open end is proximate a contacting surface of said polisher.

16. A tooth polishing assembly as recited in claim 15, further comprising:
a pair of polishers and a pair of polisher gears.

17. A tooth polishing assembly as recited in claim 16, wherein:
said splatter guard is provided in an oval shape encompassing said pair of polishers.

18. A tooth polishing assembly as recited in claim 15, further comprising:
a pair of polishers comprising a first polisher and a second polisher, wherein said first polisher is provided in a first polisher form factor and a second polisher is provided in a second polisher form factor, wherein said first polisher form factor and said second polisher form factor are dissimilar.

19. A tooth polishing assembly as recited in claim 18, wherein said first polisher form factor is a prophy cup and said second polisher form factor is a polisher brush.

20. A tooth polishing assembly as recited in claim 15, further comprising a power source integrated into said prophy angle drive assembly.

* * * * *